(12) United States Patent
Jadhav et al.

(10) Patent No.: US 10,080,600 B2
(45) Date of Patent: Sep. 25, 2018

(54) MONOPOLAR ELECTRODE WITH SUCTION ABILITY FOR CABG SURGERY

(71) Applicant: COVIDIEN LP, Mansfield, MA (US)

(72) Inventors: Amarsinh D. Jadhav, Islampur (IN); Mushtaque Syed Ahmed, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 708 days.

(21) Appl. No.: 14/601,472

(22) Filed: Jan. 21, 2015

(65) Prior Publication Data

US 2016/0206361 A1    Jul. 21, 2016

(51) Int. Cl.
| | | |
|---|---|---|
| A61B 18/08 | (2006.01) | |
| A61B 18/14 | (2006.01) | |
| A61B 18/00 | (2006.01) | |

(52) U.S. Cl.
CPC .......... *A61B 18/08* (2013.01); *A61B 18/1402* (2013.01); *A61B 18/1482* (2013.01); *A61B 2018/00351* (2013.01); *A61B 2018/1432* (2013.01); *A61B 2218/008* (2013.01)

(58) Field of Classification Search
CPC ......... A61B 18/08; A61B 18/10; A61B 18/12; A61B 18/14; A61B 18/1402; A61B 18/1442; A61B 18/1445; A61B 18/1448; A61B 2018/00351; A61B 2018/1432; A61B 2218/008
USPC ..................................................... 606/28–50
See application file for complete search history.

(56) References Cited

U.S. PATENT DOCUMENTS

| | | |
|---|---|---|
| D223,367 S | 4/1972 | Kountz |
| D263,020 S | 2/1982 | Rau, III |
| D266,842 S | 11/1982 | Villers et al. |
| D278,306 S | 4/1985 | McIntosh |
| 4,683,884 A | 8/1987 | Hatfield et al. |
| 4,719,914 A | 1/1988 | Johnson |
| D295,893 S | 5/1988 | Sharkany et al. |

(Continued)

FOREIGN PATENT DOCUMENTS

| | | |
|---|---|---|
| CN | 1103807 A | 6/1995 |
| DE | 390937 C | 3/1924 |

(Continued)

OTHER PUBLICATIONS

European Search Report for EP 15 19 1725 dated Jun. 16, 2016.

(Continued)

*Primary Examiner* — Michael Peffley
*Assistant Examiner* — Khadijeh Vahdat

(57) ABSTRACT

An elongated electrode includes a proximal conductor, a tubular member, and a treatment portion. The tubular member defines a channel therethrough and has proximal and distal end portions. The proximal end portion receives the proximal conductor within a portion of the channel and defines a hole through an inner and outer surface of the tubular member in fluid communication with the channel. The treatment portion is coupled to the distal end portion of the tubular member and includes a base and an arm extending distally from the base. The base defines a port in fluid communication with the channel of the tubular member. The arm is in electrical communication with the proximal conductor and is configured to deliver electrosurgical energy to tissue.

18 Claims, 6 Drawing Sheets

(56) References Cited

U.S. PATENT DOCUMENTS

| | | | |
|---|---|---|---|
| D295,894 S | 5/1988 | Sharkany et al. | |
| 5,195,959 A | 3/1993 | Smith | |
| 5,348,555 A | 9/1994 | Zinnanti | |
| D354,218 S | 1/1995 | Van de Peer | |
| 5,413,575 A | 5/1995 | Haenggi | |
| 5,800,431 A | 9/1998 | Brawn | |
| 5,830,214 A | 11/1998 | Flom et al. | |
| D424,693 S | 5/2000 | Pruter | |
| D424,694 S | 5/2000 | Tetzlaff et al. | |
| D425,201 S | 5/2000 | Tetzlaff et al. | |
| 6,258,088 B1 | 7/2001 | Tzonev et al. | |
| 6,293,945 B1 | 9/2001 | Parins et al. | |
| D449,886 S | 10/2001 | Tetzlaff et al. | |
| 6,312,441 B1 | 11/2001 | Deng | |
| 6,371,955 B1 * | 4/2002 | Fuimaono | A61B 18/1492 606/29 |
| D457,958 S | 5/2002 | Dycus et al. | |
| D457,959 S | 5/2002 | Tetzlaff et al. | |
| 6,530,924 B1 | 3/2003 | Ellman et al. | |
| 6,558,379 B1 * | 5/2003 | Batchelor | A61B 18/1482 604/21 |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,329,253 B2 | 2/2008 | Brounstein et al. | |
| RE40,156 E | 3/2008 | Sharps et al. | |
| D564,662 S | 3/2008 | Moses et al. | |
| 7,367,975 B2 | 5/2008 | Malecki et al. | |
| D576,932 S | 9/2008 | Strehler | |
| 7,462,178 B2 | 12/2008 | Woloszko et al. | |
| 7,537,594 B2 | 5/2009 | Sartor | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,828,797 B2 | 11/2010 | Eggers | |
| 7,840,253 B2 | 11/2010 | Tremblay et al. | |
| D634,010 S | 3/2011 | DeCarlo | |
| 8,038,669 B2 | 10/2011 | Malecki et al. | |
| 8,057,470 B2 | 11/2011 | Lee et al. | |
| 8,323,279 B2 * | 12/2012 | Dahla | A61B 18/1402 604/30 |
| D681,810 S | 5/2013 | DeCarlo | |
| 8,808,287 B2 | 8/2014 | Heard et al. | |
| 2005/0004634 A1 | 1/2005 | Ricart et al. | |
| 2006/0095027 A1 | 5/2006 | Eggers | |
| 2006/0095034 A1 * | 5/2006 | Garito | A61B 17/32002 606/45 |
| 2007/0060989 A1 | 3/2007 | Deem et al. | |
| 2007/0299435 A1 | 12/2007 | Crowe et al. | |
| 2011/0077645 A1 | 3/2011 | Lin | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| EP | 2438876 A1 | 4/2012 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |

(56) References Cited

FOREIGN PATENT DOCUMENTS

| SU | 727201 A2 | 4/1980 |
|---|---|---|
| WO | 00/36985 A2 | 6/2000 |
| WO | 2010/035831 A1 | 4/2010 |

OTHER PUBLICATIONS

U.S. Appl. No. 14/242,019, filed Apr. 1, 2014; inventor: Brannan.
U.S. Appl. No. 14/242,048, filed Apr. 1, 2014; inventor: Prakash.
U.S. Appl. No. 14/281,264, filed May 19, 2014; inventor: Prakash.
U.S. Appl. No. 14/281,344, filed May 19, 2014; inventor: Shiu.
U.S. Appl. No. 14/300,824, filed Jun. 10, 2014; inventor: Behnke.
U.S. Appl. No. 14/300,871, filed Jun. 10, 2014; inventor: Bonn.
U.S. Appl. No. 14/306,865, filed Jun. 17, 2014; inventor: Brannan.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radial, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hernorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.
U.S. Appl. No. 14/011,414, filed Aug. 27, 2013; inventor: Ohri.
U.S. Appl. No. 14/011,438, filed Aug. 27, 2013; inventor: Ohri.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSureTM " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.

Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

\* cited by examiner

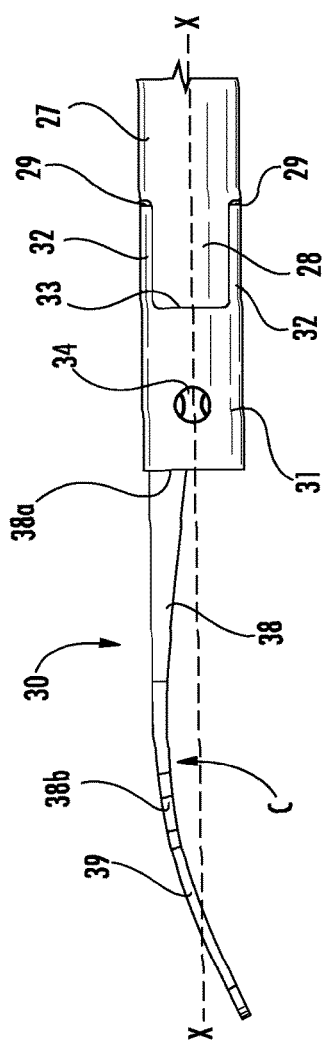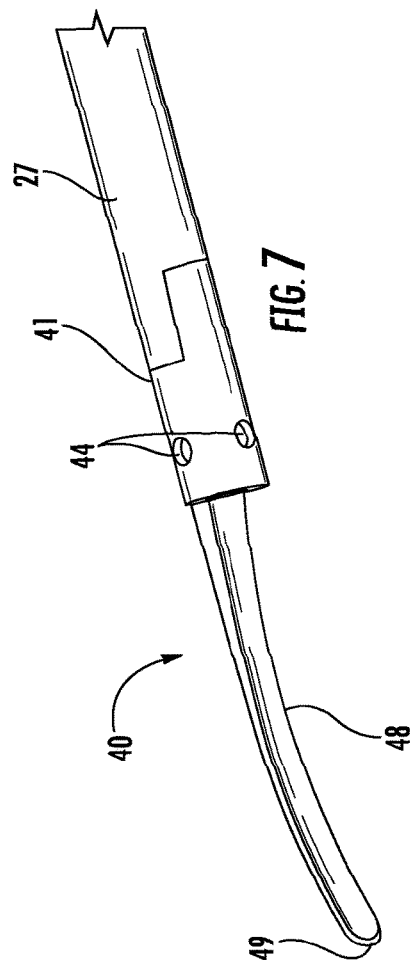

MONOPOLAR ELECTRODE WITH SUCTION ABILITY FOR CABG SURGERY

BACKGROUND

1. Technical Field

The present disclosure relates generally to electrosurgical instruments and, more particularly, to electrosurgical instruments with elongated electrodes and evacuation assemblies.

2. Discussion of Related Art

Electrosurgical instruments which treat tissue and have provisions for evacuating fluid and/or smoke have been available for some time. Typically, a combination electrosurgery and suction device is employed wherever excessive fluid or smoke must be removed from the operative site in order to successfully perform the desired procedure. Generally, these devices include a housing or handle having an electrode extending from a distal end thereof, and a suction port disposed in proximity to the electrode to evacuate fluid and/or smoke. A suction source is attached to the instrument for evacuating excess fluid, debris, smoke, vapors, etc. from the surgical site through the suction port. The electrode is operably coupled to a source of electrosurgical energy, such as an electrosurgical generator.

Such electrosurgical instruments may be used during a Corornary Artery Bypass (CABG) procedure. Generally, CABG procedures are performed by opening the chest cage to access a chest cavity of a patient (i.e., accessing the chest cavity from the center of the chest). CABG procedures may also be performed by accessing the chest cavity between ribs in the chest-side without requiring the chest cage to be opened. To perform CABG procedures through the chest-side the electrosurgical instruments must be elongated to reach the surgical site within the chest cavity.

Accordingly, there is a need for electrosurgical instruments that may be used on tissue and which evacuate fluid and/or smoke using elongated electrodes and suction ports in the proximity of the electrode.

SUMMARY

In an aspect of the present disclosure, an elongated electrode includes a proximal conductor, a tubular member, and a treatment portion. The tubular member defines a channel and includes proximal and distal end portions. The proximal end portion receives the proximal conductor within a portion of the channel defined therein and defines a hole through inner and outer surfaces of the tubular member which are in fluid communication with the channel. The treatment portion is coupled to the distal end portion of the tubular member and includes a base and an arm extending distally from the base. The base defines a port in fluid communication with the channel of the tubular member. The arm is in electrical communication with the proximal conductor and the treatment portion is configured to deliver electrosurgical energy to tissue.

In some aspects, the port is defined in a sidewall of the base. The base may define a plurality of ports defined in a sidewall of the base and in fluid communication with the channel of the tubular member.

Additionally or alternatively, the port may be defined in a distal end surface of the base. The arm may be coupled to the base about the port. The arm may define an arched surface about a longitudinal axis of the base and may define a curvature along the longitudinal axis of the base. The arm may include a tip that passes through the longitudinal axis of the base. The tip may splay out from the arm to define a spatula tip. The base and the arm of the treatment portion may be coated with a dielectric material.

In certain aspects, the tubular member has a length in a range of 15 cm to 45 cm from a proximal end to a distal end thereof. The tubular member may have a diameter in a range of 2.0 mm to 10.0 mm.

In another aspect of the present disclosure, an electrosurgical dissection system includes an evacuation attachment, an electrosurgical instrument, and an elongated electrode. The evacuation attachment includes a body and a distal end portion which define a passage therethrough. The electrosurgical instrument is coupled to the body of the evacuation attachment and includes a distal end that is received within the distal end portion of the evacuation attachment. The electrosurgical instrument includes an electrode connector. The elongated electrode may be any of the elongated electrodes disclose herein and includes a proximal conductor, a tubular member, and a treatment portion. The proximal conductor has a proximal end that is received within the electrode connector of the electrosurgical instrument. The tubular member defines a channel therethrough and has proximal and distal end portions. The proximal end portion receives the proximal conductor within a portion of the channel defined therein. The proximal end portion defines a hole through inner and outer surfaces of the tubular member that is in fluid communication with the channel. The proximal end portion of the tubular member is received within the distal end portion of the evacuation attachment such that the channel of the tubular member is in fluid communication with the passage of the evacuation attachment through the hole. The treatment portion is coupled to the distal end portion of the tubular member and includes a base and an arm extending distally from the base. The base portion defines a port in fluid communication with the channel of the tubular member. The arm is in electrical communication with the proximal conductor and the treatment portion is configured to deliver electrosurgical energy to tissue.

In some aspects, the electrosurgical dissection system includes an electrosurgical generator in communication with the electrosurgical instrument to selectively supply electrosurgical energy to the treatment portion of the electrode. Additionally or alternatively, the electrosurgical dissection system may include a vacuum source in communication with the passage of the evacuation attachment to selectively supply suction through the port of the base portion.

In certain aspects, the distal end portion of the evacuation attachment defines an instrument port in communication with the passage. The instrument port may receive a distal end of the electrosurgical instrument therein.

In yet another aspect of the present disclosure, a surgical procedure includes inserting a treatment portion of an elongated electrode through a chest-side surgical site of a patient, positioning the treatment portion adjacent targeted tissue, activating an electrosurgical generator to supply electrosurgical energy to the treatment portion, and activating a vacuum source to supply suction through the treatment portion. The targeted tissue is adjacent the heart of the patient. When the electrosurgical generator is activated, the treatment portion applies electrosurgical energy to the targeted tissue. When the vacuum source is activated, liquid or gas adjacent the treatment portion is evacuated through a port in the treatment portion.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 6 is a partial top view of the distal end of the elongated electrode of FIG. 2;

FIG. 7 is a perspective view of a distal end of another elongated electrode in accordance with the present disclosure.

DETAILED DESCRIPTION

Figure 1:
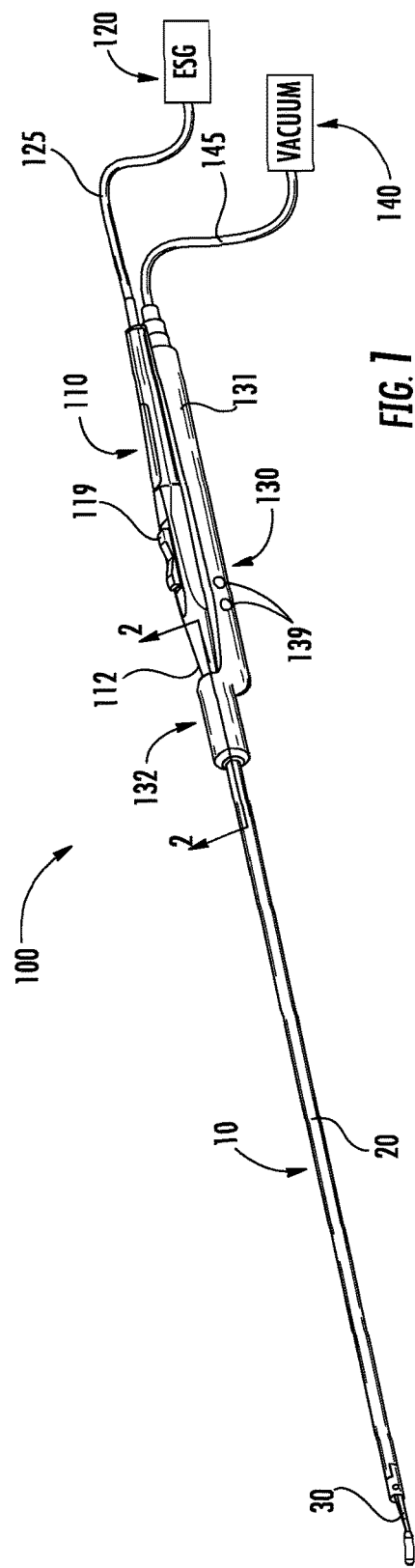
FIG. 1 is a perspective view of an illustrative embodiment of an electrosurgical dissection system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 2:
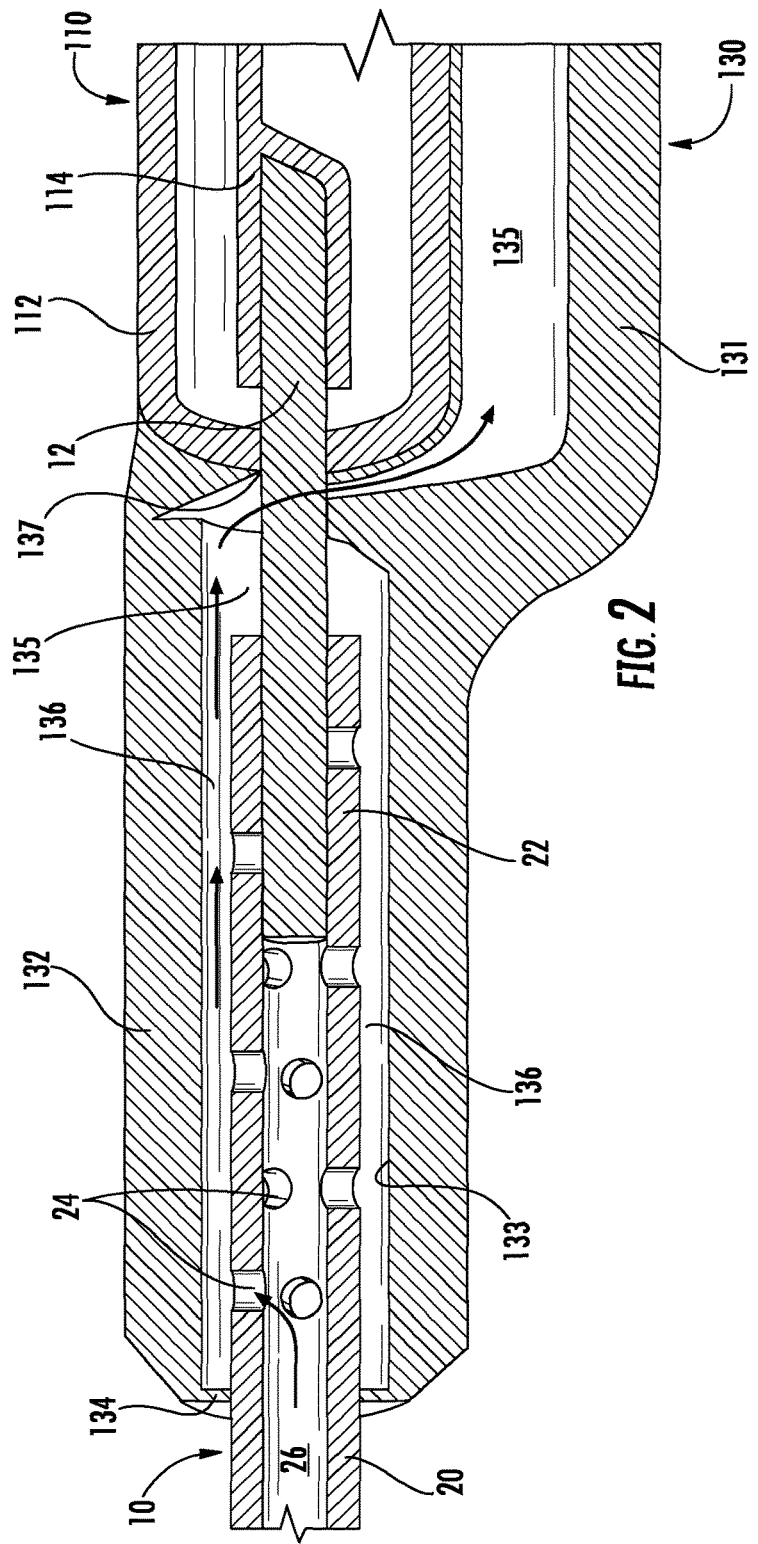
FIG. 2 is a partial side cross-sectional view taken along the section line 2-2 of FIG. 1.
Figure 3:
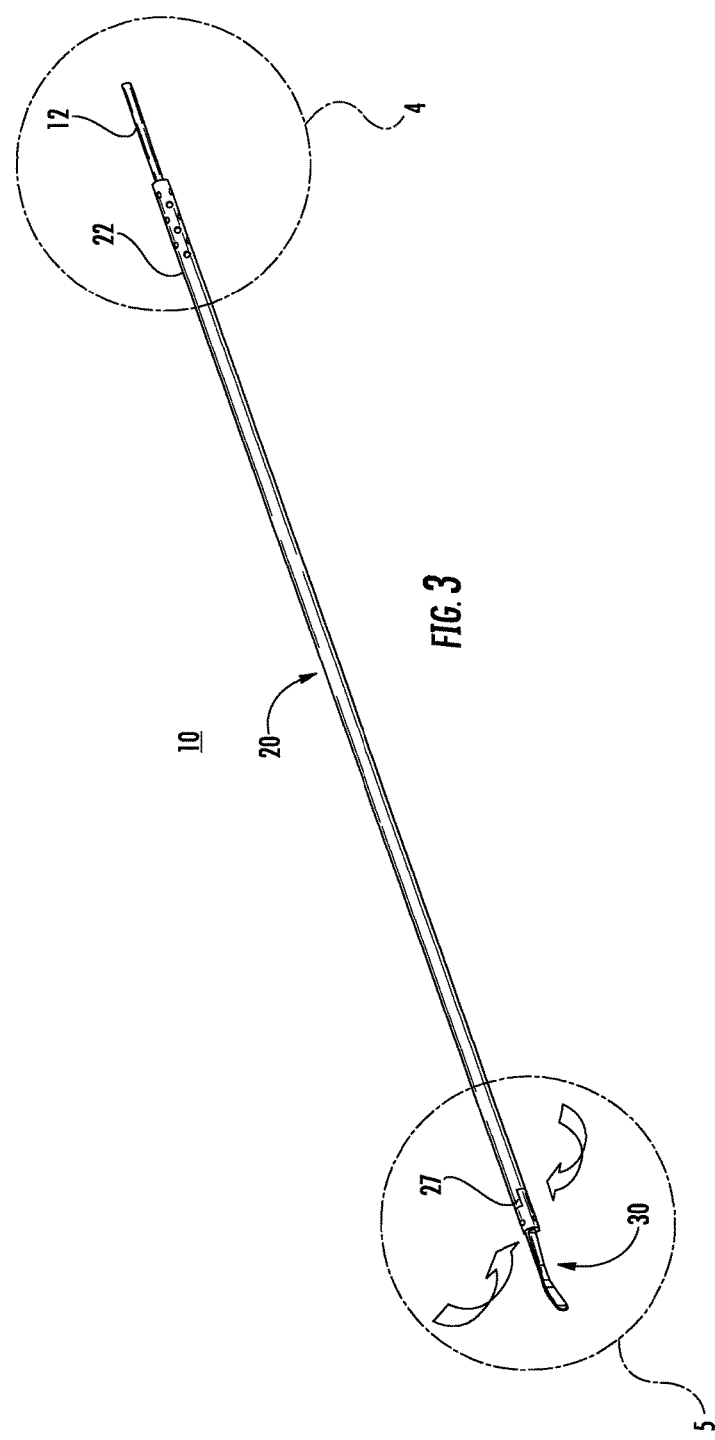
FIG. 3 is a perspective view of the elongated electrode of the electrosurgical dissection system of FIG. 1
Figure 4:
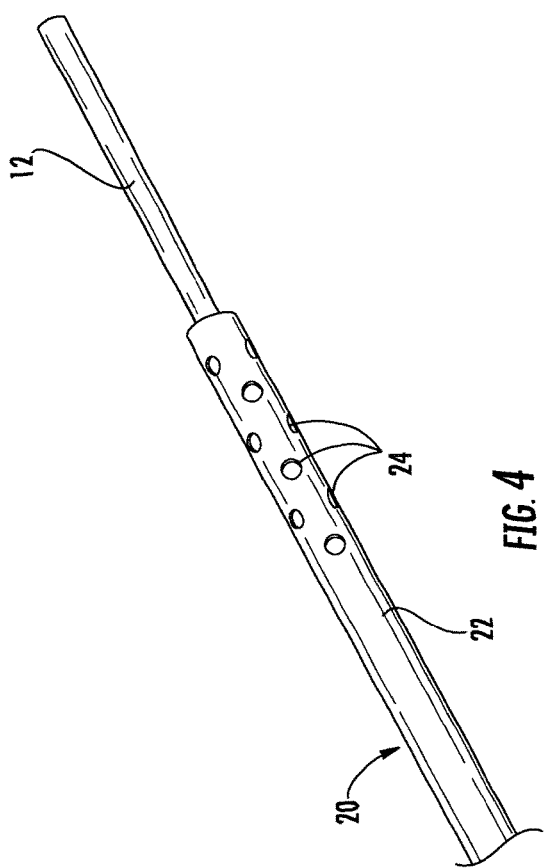
FIG. 4 is an enlarged perspective view of the indicated area of detail in FIG. 3.

Referring to FIGS. 1 and 2, an electrosurgical dissection system 100 is provided in accordance with the present disclosure and includes an elongated electrode 10, an electrosurgical instrument 110, an electrosurgical generator (ESG) 120, an evacuation attachment 130, and a vacuum source 140. As detailed below, the elongated electrode 10 is releasably coupled to the distal end of the electrosurgical instrument 110 through the evacuation attachment 130 and is adapted to apply electrosurgical energy to tissue and evacuate liquid and/or gas from a surgical site.

The electrosurgical instrument 110 is operably coupled to an electrosurgical generator 120 via a conductor 125 to provide electrosurgical energy to the electrosurgical instrument 110. The electrosurgical instrument 110 includes an actuator 119 to selectively control the delivery of the electrosurgical energy. As shown in FIG. 1, the actuator 119 is a pivotable switch; however, it is contemplated that the actuator 119 may include a variable control, such as a pressure sensor, rotary control, or slide control (not shown), that are configured to continuously vary a property of the delivered electrosurgical energy. In addition, it is contemplated that the actuator 119 may be a button, a tactile dome switch, a toggle switch, or any suitable means for activation the delivery of electrosurgical energy. As best shown in FIG. 2, the distal end 112 of the electrosurgical instrument 110 includes an electrode connector 114 that slidably couples to a proximal conductor 12 of the elongated electrode 10 to provide electrosurgical energy from the electrosurgical instrument 110 to the elongated electrode 10.

The evacuation attachment 130 is operably coupled to the vacuum source 140 by a flexible vacuum tube 145 to evacuate liquid and/or gas from a surgical site. The evacuation attachment 130 has a body 131 that is attached to the bottom of the electrosurgical instrument 110 to secure the evacuation attachment 130 to the electrosurgical instrument 110. The evacuation attachment 130 includes a distal end portion 132 that is positioned distal to the distal end 112 of the electrosurgical instrument 110. The distal end portion 132 of the evacuation attachment 130 defines an instrument opening 137 that receives the distal end 112 of the electrosurgical instrument 110 therein. The instrument opening 137 may form a seal with the distal end 112 of the electrosurgical instrument 110 and/or the proximal connector 12 of the elongated electrode 10 to prevent ingress of foreign matter (e.g., liquid or gas) into the distal end 112 of the electrosurgical instrument 110. In addition, the instrument opening 137 may form a seal with the distal end 112 of the electrosurgical instrument 110 to increase suction passing through the evacuation attachment 130 to the elongated electrode 10 as detailed below. The body 131 defines a passage 135 that is in communication with the lumen 145 for the evacuation of liquid and/or gas through the evacuation attachment 130. The instrument opening 137 may be in fluid communication with the passage 135 of the evacuation attachment 130.

The evacuation attachment 130 includes a suction control 139, such as a pushbutton (e.g., for on/off operation) as is shown in FIG. 1, and/or may include a variable control, such as a pressure sensor, rotary control, or slide control (not shown), that is configured to continuously vary the amount of suction. It is also contemplated that the suction control 139 may be disposed on or adjacent the vacuum source 140. In addition, it is contemplated that the suction control 139 may be a pivoting switch, a tactile dome switch, a toggle switch, or any suitable means for activation the vacuum source 140.

Exemplary electrosurgical instruments and evacuation attachments are disclosed in commonly owned and co-pending U.S. Provisional Patent Application Ser. No. 62/001,186 filed on May 21, 2014 and titled "Multipurpose Electrosurgical Instrument with Telescoping Aspiration Cannula," the entire contents of which are hereby incorporated by reference.

With reference to FIGS. 2-6, the elongated electrode 10 includes the proximal conductor 12, a tubular member 20, and a treatment portion 30. The proximal conductor 12 passes through the distal end portion 132 of the evacuation attachment 130 and into the distal end 112 of the electrosurgical instrument 110 to electrically couple the elongated electrode 10 to the ESG 120. The proximal conductor 12 is received within the electrode connector 114 of the electrosurgical instrument 110. It is contemplated that the proximal conductor 12 may be received within the connector 114 via a friction fit or a bayonet type connection. Additionally, or alternatively, the tubular member 20 may form a bayonet type connection with the distal end portion 132 of the evacuation attachment to secure the proximal conductor 12 within the electrode connector 114.

The tubular member 20 defines a channel 26 therethrough for the passage of evacuated liquid and/or gas. A proximal end portion 22 of the tubular member 20 receives the proximal conductor 12 within the channel 26. The tubular member 20 may receive the proximal conductor 12 within the channel 26 in a sealing relationship. The proximal conductor 12 is coupled to the tubular member 20 by any suitable mean including, but not limited to, welding, gluing, a friction fit, or a combination thereof. It will be appreciated that the proximal conductor 12 is constructed from a conductive material (e.g., stainless steel, copper, gold, mild steel, steel alloys, aluminum, aluminum alloys, magnesium, and magnesium alloys).

The proximal end portion 22 of the tubular member 20 is disposed within the distal end portion 132 of the evacuation attachment 130. In addition, the proximal end portion 22 may be sized and dimensioned to form a sealing relationship with a distal opening 134 of the evacuation attachment 130. The tubular member 20 and an inner surface 133 of the distal end portion 132 of the evacuation attachment 130 define a gap 136 of the passage 135 therebetween. The proximal end portion 22 defines holes 24 through the surface thereof to provide communication between the channel 26 of the tubular member 20 and the gap 136 of the passage 135 of the attachment member 130 such that liquid and/or gas can be evacuated from the channel 26, through the holes 24, and into the passage 135. With particular reference to FIG. 2, the proximal conductor 12 may at least partially occlude one or more of the holes 24.

The tubular member 20 may be formed from material having optically-transparent properties, for example, and without limitation, polycarbonate, to allow a clinician to visually monitor the aspiration or evacuation process detailed below. This, in turn, enables the clinician to detect blockages, quantitatively and qualitatively assess evacuated material, and to improve the effectiveness of the procedure and of the dissection system 100. The tubular member 20 may include an inner surface that is polished and/or includes a transparent coating, such as a hydrophobic and/or oleophobic coating that is adapted to repel evacuated materials (e.g., liquid and/or gas) to promote visual clarity and/or improve the flow of evacuated materials. In embodiments, the tubular member 20 may include a lubricious coating, such as, without limitation, polytetrafluoroethylene (PTFE). One such PTFE coating is sold under the brand name Teflon® and is available from E. I. du Pont de Nemours and Company or its affiliates. The lubricious coating may be transparent and/or applied in a manner so as to render the lubricious coating effectively transparent, such as, without limitation, nano-coating.

The tubular member 20 has a length in a range of about 15 cm to about 45 cm, e.g., 35 cm, from the proximal end portion 22 to the distal end portion 27 such that the overall length of the elongated electrode is in a range of about 20 cm to about 50 cm, e.g., 40 cm, from a proximal end of the proximal connector 12 to a tip 39 of the treatment portion 30. The tubular member 20 has an outer diameter in the range of about 2.0 mm to about 10.0 mm, e.g., 4.8 mm.

Figure 5:
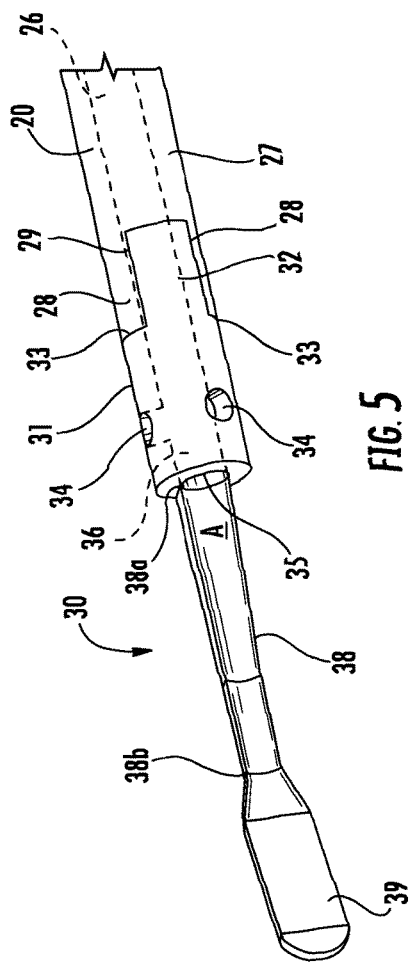
FIG. 5 is an enlarged perspective view of the indicated area of detail in FIG. 3.

Referring now to FIG. 5, the tubular member 20 extends to a distal end portion 27 that couples to the treatment portion 30. The distal end portion 27 includes fingers 28 that extend towards the treatment portion 30 and defines recesses 29 radially between the fingers 28. The treatment portion 30 includes fingers 32 that extend towards the tubular member 20 and defines recesses 33 radially between the fingers 32. The fingers 28 of the distal end portion 27 are received in the recesses 33 of the treatment portion 30 and the fingers 32 of the treatment portion 30 are received in the recesses 29 of the distal end portion 27. The distal end portion 27 is coupled to the treatment portion 30 by any suitable mean including, but not limited to, welding, gluing, a friction fit, or a combination thereof. For example, the distal end portion 27 may be coupled to the treatment portion 30 by welding along the mating lines between the fingers 28, 32 and the recesses 29, 33.

The treatment portion 30 is configured to apply electrosurgical energy from the ESG 120 (FIG. 1) to tissue. The treatment portion 30 includes a cylindrical base 31, an arm 38 extending from the base 31, and a tip 39 at the distal end of the arm 38. The base 31 is sized and dimensioned to form a smooth transition with the tubular member 20 and defines a channel 36 in communication with the channel 26 (FIG. 2) of the tubular member 20. The base 31 defines side ports 34 through an outer circumference thereof which are in communication with the passage 36. As shown, the side ports 34 have a constant circular shaped cross-section; however, it is contemplated that the cross-section of the side ports 34 may define other shapes (e.g., elliptical, rectangular, hexagonal) and/or may have a varying cross-section from adjacent the channel 36 to the outer circumference of the base 31 (e.g., the side ports 34 may taper to form a conical or frustoconical shape). The base 31 also defines a distal port 35 in a distal end surface thereof that is in communication with the channel 36. The side ports 34 and the distal port 35 are configured to evacuate liquid and/or gas from a surgical site adjacent the treatment portion 30 through the channels 26, 36. The ports 34, 35 may be shaped to evacuate liquid and/or gas adjacent the arm 38 and the tip 39. It will be appreciated that the treatment portion 30 is constructed from a conductive material (e.g., stainless steel, copper, gold, mild steel, steel alloys, aluminum, aluminum alloys, magnesium, and magnesium alloys).

With additional reference to FIG. 6, the arm 38 is coupled at a proximal end 38a to the cylindrical base 31 and at a distal end 38b to the tip 39. The proximal end 38a of the arm 38 is coupled to the distal end surface of the cylindrical base 31 to define an arched surface "A" in a plane orthogonal to a longitudinal axis X-X of the cylindrical base 31. The arched surface "A" of the arm 38 may direct liquid and/or gas into the distal port 35. In addition, the arm 38 defines a curvature "C" along the longitudinal axis X-X from the proximal end 38a to the distal end 38b and may define the curvature "C" through the distal end of the tip 39. The curvature "C" may be constant or varying along the length of the arm 38 and/or tip 39 such that the distal port 35 is substantially unrestricted and a longitudinal axis X-X of the treatment portion 30 and the tubular member 20 passes through the tip 39. It is also contemplated that the distal end of the tip 39 may be positioned along the longitudinal axis X-X. The curvature "C" of the arm 38 may allow for better visibility of the surgical site during a surgical procedure as detailed below. The arm 38 and the cylindrical base 31 may be of monolithic construction or the arm 38 may be coupled to the cylindrical base 31 by any suitable mean including, but not limited to, welding, gluing, or a combination thereof. The arm 38 and the tip 39 may be of monolithic construction or the tip 39 may be coupled to the arm 38 by any suitable mean including, but not limited to, welding, gluing, or a combination thereof. It is contemplated that portions of the treatment portion 30 (e.g., the base 31 or the arm 38) may be coated with a dielectric material to prevent electrosurgical energy from being applied by these portions of the treatment portion 30.

The tip 39 is in selective electrical communication with the ESG 120 to apply electrosurgical energy to tissue. Specifically, as detailed above, the instrument 110 is electrically coupled to the ESG 120 via a conductor 125 and is configured to selectively conduct electrosurgical energy from the ESG 120 to the electrode connector 114 in response to activation of actuator 119. The proximal conductor 12 of the elongate electrode 10 is coupled to the electrode connector 114 to electrically couple the elongate electrode 10 to the ESG 120. The treatment portion 30 is in electrical communication with the proximal conductor 12 by any suitable means including, but not limited to, a conductive lining along the inner surface of the tubular member 20, a conductor disposed within the passage 26 of the tubular member 20, a conductor disposed within a wall of the tubular member 20, or a trace disposed along the inner surface of the tubular member 20.

With continued reference to FIG. 5, the tip 39 extends from the arm 38 and splays outward therefrom to form a spatula tip. The tip 39 may be arched about the longitudinal axis X-X and/or may define a curvature along the longitudinal axis X-X as detailed above with respect to the arm 38.

In an aspect of the present disclosure, the electrosurgical dissection system 100 is assembled by attaching the evacuation attachment 130 to the electrosurgical instrument 110. To attach the evacuation attachment 130 to the electrosurgical instrument 110, the distal end 112 of the electrosurgical instrument 110 is inserted into the distal end portion 132 of the evacuation attachment 130 such that the distal end 112 of the electrosurgical instrument 112 is received within the instrument opening 137 (FIG. 2) of the distal end portion 132. The body 131 of the evacuation attachment 130 is configured to couple to the body 111 of the electrosurgical instrument 110. The proximal conductor 12 of the elongated electrode 10 is then passed through the distal opening 134 and the distal end portion 132 of the evacuation attachment 130 and into the electrode connector 114 of the electrosurgical instrument 110 such that the proximal conductor 12 is in electrical communication with the electrode connector 114. As detailed above, the proximal conductor 12 may include a bayonet type connection to secure the proximal conductor 12 to the electrode connector 114. In such embodiments, the tubular member 20 is twisted to secure the proximal conductor 12 to the electrode connector 114. It will be appreciated that when the proximal conductor 12 is in electrical communication with the electrode connector 114, the treatment portion 30 of the elongated electrode 10 is in electrical communication with the electrode connector 114 of the electrosurgical instrument 110.

In addition, as the proximal conductor 12 is received within the electrical connector 114, the proximal end portion 22 of the tubular member 20 is inserted into the passage 135 of the evacuation attachment 130 such that the channel 26 of the tubular member 20 is in fluid communication with the passage 135 through the holes 24. As detailed above, the distal end 134 of the evacuation attachment 130 may form a seal around the outer surface of the tubular member 120 to form a distal end of the passage 135.

When the electrosurgical instrument 110 and the evacuation attachment 130 are coupled together, the electrosurgical instrument 110 is coupled to the ESG 120 to selectively provide electrosurgical energy to electrode connector 114 in response to activation of the actuator 119 and the evacuation attachment 130 is coupled to the vacuum source 140 such that suction may be applied though the passage 135 of the evacuation attachment 130 in response to activation of the actuator 139.

Referring to FIG. 7, another illustrative embodiment of a treatment portion is shown as treatment portion 40. The treatment portion 40 is substantially similar to the treatment portion 30 detailed above and functions in a substantially similar manner, as such only the differences between the treatment portion 40 and the treatment portion 30 will be detailed below. The treatment portion 40 includes a cylindrical base 41 and an arm 48 extending distally from the cylindrical base 41. The arm 48 includes a tip 49 at a distal end thereof. The arm 48 transitions into the tip 49 in a relatively smooth manner and is integrally formed with the arm 48. Similar to arm 38 detailed above, the arm 48 is arched about to a longitudinal axis of the treatment portion 40 and defines a curvature along the longitudinal axis.

Figure 8:
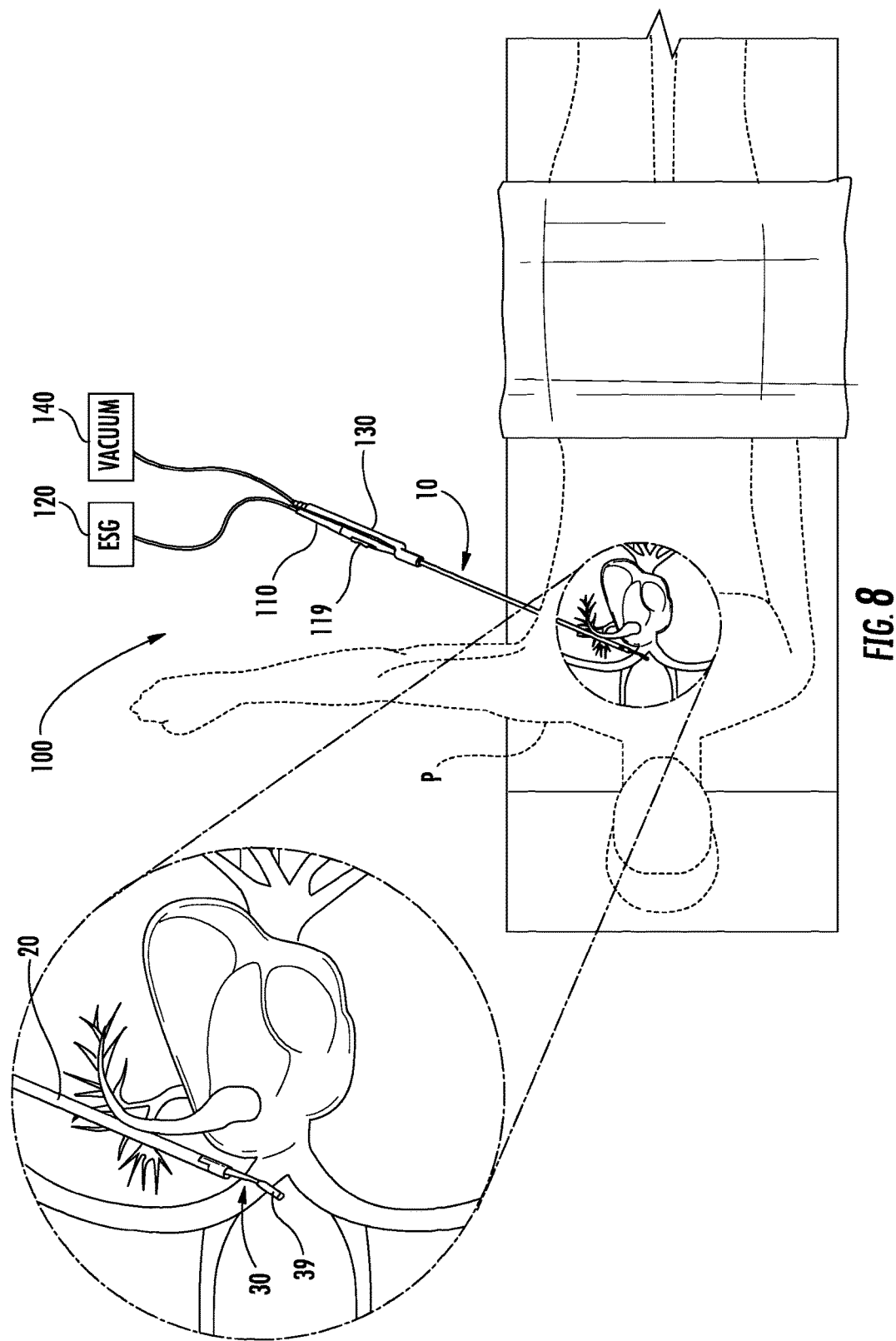
FIG. 8 is a perspective view of the electrosurgical dissection system of FIG. 1 inserted in the chest-side of a patient and a cut-away view of the chest cavity of the patient.

In use, referring to FIG. 8, with the electrosurgical dissection system 100 assembled, the elongated electrode 10 is inserted through an incision in a chest-side of a patient until the treatment portion 30 is at a desired position within a surgical site (i.e., adjacent or in contact with targeted tissue). With the treatment portion 30 in the desired position, the actuator 139 (FIG. 1) is activated to provide suction through the side and distal ports 34, 35 (FIG. 5) of the treatment portion 30. Then the actuator 119 is activated to apply electrosurgical energy to the targeted tissue with the tip 39 of the treatment portion 30. As electrosurgical energy is applied to the targeted tissue, liquid and/or gases may be generated (e.g., blood and/or smoke). The suction provided through the side and distal ports 34, 35 draws the liquid and/or gases through the side and distal ports 34, 35, the channels 26, 36 of the base 31 and the tubular member 20, and the passage 135 (FIG. 2) of the evacuation attachment 130. By evacuating the liquid and/or gases from the surgical site, visibility may be improved during the surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. An elongated electrode, comprising:
   a proximal conductor defining a longitudinal axis;
   a tubular member disposed coaxially about the longitudinal axis and defining a channel therethrough, the tubular member having proximal and distal end portions, the proximal end portion receiving the proximal conductor within a proximal portion of the channel, the proximal conductor sealing the proximal portion of the channel, the proximal end portion defining a hole through inner and outer surfaces of the tubular member in fluid communication with the channel; and
   a treatment portion coupled to the distal end portion of the tubular member, the treatment portion including a base and an arm extending distally from the base, the base defining a port in fluid communication with the channel of the tubular member, the arm in electrical communication with the proximal conductor, the treatment portion configured to deliver electrosurgical energy to tissue.

2. The elongated electrode of claim 1, wherein the port is defined in a sidewall of the base.

3. The elongated electrode of claim 2, wherein the base defines a plurality of ports defined in a sidewall of the base and in fluid communication with the channel of the tubular member.

4. The elongated electrode of claim 1, wherein the port is defined in a distal end surface of the base.

5. The elongated electrode of claim 4, wherein the arm is coupled to the base about the port.

6. The elongated electrode of claim 5, wherein the arm defines an arched surface about a longitudinal axis of the base.

7. The elongated electrode of claim 5, wherein the arm defines a curvature along the longitudinal axis of the base.

8. The elongated electrode of claim 7, wherein the arm includes a tip that passes through the longitudinal axis of the base.

9. The elongated electrode of claim 8, wherein the tip splays out from the arm to define a spatula tip.

10. The elongated electrode of claim 1, wherein the tubular member has a length in a range of 20 cm to 50 cm from a proximal end to a distal end thereof.

11. The elongated electrode of claim 1, wherein the tubular member has a diameter in a range of 2.0 mm to 10.0 mm.

12. The elongated electrode of claim 1, wherein the base and the arm of the treatment portion are coated with a dielectric material.

13. An electrosurgical dissection system, comprising:
   an evacuation attachment including a body and a distal end portion, the distal end portion and the body defining a passage therethrough;
   an electrosurgical instrument coupled to the body of the evacuation attachment and including a distal end received within the distal end portion of the evacuation attachment, the electrosurgical instrument including an electrode connector; and
   an elongated electrode defining a longitudinal axis and including:
      a proximal conductor having a proximal end received within the electrode connector of the electrosurgical instrument, the proximal conductor positioned along the longitudinal axis;
      a tubular member disposed coaxially about the longitudinal axis and defining a channel therethrough, the tubular member having proximal and distal end portions, the proximal end portion receiving the proximal conductor within a proximal portion of the channel, the proximal conductor sealing the proximal portion of the channel, the proximal end portion defining a hole through inner and outer surfaces of the tubular member in fluid communication with the channel, the proximal end portion of the tubular member received within the distal end portion of the evacuation attachment such that the channel of the tubular member is in fluid communication with the passage of the evacuation attachment through the hole; and
      a treatment portion coupled to the distal end portion of the tubular member, the treatment portion including a base and an arm extending distally from the base, the base portion defines a port in fluid communication with the channel of the tubular member, the arm in electrical communication with the proximal conductor and the treatment portion configured to deliver electrosurgical energy to tissue.

14. The electrosurgical dissection system of claim 13, further comprising an electrosurgical generator in communication with the electrosurgical instrument to selectively supply electrosurgical energy to the treatment portion of the electrode.

15. The electrosurgical dissection system of claim 13, further comprising a vacuum source in communication with the passage of the evacuation attachment to selectively supply suction through the port of the base portion.

16. The electrosurgical dissection system of claim 13, wherein the port is defined in a distal end surface of the base and the base defines at least one side port in an outer surface of the base in fluid communication with the channel of the tubular member.

17. The electrosurgical dissection system of claim 13, wherein the distal end portion of the evacuation attachment defines an instrument port in communication with the passage, the instrument port receiving a distal end of the electrosurgical instrument therein.

18. The electrosurgical dissection system of claim 13, wherein the proximal conductor is slidably received within the electrode connector of the electrosurgical instrument.

* * * * *